United States Patent [19]

Child

[11] 4,252,525
[45] Feb. 24, 1981

[54] DENTAL IMPLANT

[76] Inventor: Frank W. Child, Eagle Bend, Minn. 56446

[21] Appl. No.: 104,156

[22] Filed: Dec. 17, 1979

Related U.S. Application Data

[63] Continuation-in-part of Ser. No. 877,073, Feb. 13, 1978, Pat. No. 4,195,409.

[51] Int. Cl.³ .............................................. A61C 8/00
[52] U.S. Cl. .................................. 433/173; 433/174; 433/201
[58] Field of Search ................ 433/173, 174, 175, 201

[56] References Cited

U.S. PATENT DOCUMENTS

| | | | |
|---|---|---|---|
| 2,069,112 | 1/1937 | Oppenheim | 128/409 |
| 2,121,875 | 6/1938 | Kruse et al. | 204/24 |
| 2,210,424 | 8/1940 | Morrison | 433/17 |
| 2,276,623 | 3/1942 | Meiman | 433/32 |
| 2,355,231 | 8/1944 | Moore | 128/172.1 |
| 2,380,468 | 7/1945 | Saffir | 433/169 |
| 2,655,922 | 10/1953 | Knappwost | 128/409 |
| 2,880,508 | 4/1959 | Lester et al. | 433/1 |
| 3,019,787 | 2/1962 | Simmons | 128/172.1 |
| 3,314,420 | 4/1967 | Smith et al. | 433/201 |
| 3,526,605 | 9/1970 | Bokros et al. | 3/1 |
| 3,605,123 | 9/1971 | Hahn | 433/173 |
| 3,707,006 | 12/1972 | Bokros et al. | 433/173 |
| 3,722,094 | 3/1973 | Rivoir | 433/169 |
| 3,727,240 | 3/1973 | Child | 128/334 R |
| 3,808,606 | 5/1974 | Tronzo | 433/175 |
| 3,855,638 | 12/1974 | Pilliar | 433/201 |
| 3,863,344 | 2/1975 | Pillet | 433/173 |
| 3,934,347 | 1/1976 | Lash et al. | 433/173 |
| 3,964,477 | 6/1976 | Ellis et al. | 128/172.1 |
| 3,971,134 | 7/1976 | Bokros | 433/176 |
| 4,014,095 | 3/1977 | Heimansohn | 433/212 |
| 4,027,393 | 6/1977 | Ellis et al. | 433/173 |
| 4,055,862 | 11/1977 | Farling | 3/1.91 |
| 4,126,937 | 11/1978 | Ellis et al. | 433/228 |
| 4,175,565 | 11/1979 | Chiarenza et al. | 433/176 |
| 4,179,809 | 12/1979 | Fagan et al. | 433/176 |

OTHER PUBLICATIONS

"Dental Implants", p. 6.
"Coming: New Plug in Teeth", Popular Science, Nov. 1977, p. 21.
"Porous Metal Bone Replacements", College of Engineering PERSPECTIVE, Univ. of Wisconsin, vol. 3, No. 6, Oct. 1976.
Silver by C. M. Gruber, Ph.D., M.D., The Cyclopedia of Medicine, Surgery, Specialties, vol. XII, p. 693.
Germicides, Fungicides, and Ectoparasiticides, by Louis S. Goodman, M.A., M.D. and Alfred Gilman Ph.D., The Pharmacological Basis of Therapeutics, p. 1105.
"Our Mightiest Germ Fighter", Science Digest, Mar. 1978, pp. 57-60.
AADR Abstracts, 1977, No. 572, p. B195, "Theoretical Biophysics", Biophysical Journal, vol. 25, p. 217a.

Primary Examiner—Robert Peshock
Attorney, Agent, or Firm—Burd, Bartz & Gutenkauf

[57] ABSTRACT

A tooth prothesis located in a mandible tooth socket having a root supporting a crown. The root has a cone-shaped head located in a recess in the bottom of the crown and a stem extended into the socket. An elastic body of ethylene vinyl acetate (EVA) copolymer surrounds and is bonded to the stem. The outer surface of the elastic body is bonded to the inside surface of a porous fabric which permits bone ingrowth to anchor the prothesis to the mandible. The fabric has a Pyrolite carbon outer skin. The upper edge of the fabric is spaced from the crown and head whereby the elastic body allows limited movement of the crown relative to the fabric. A plurality of bands of silver surround the body adjacent the lower edge of the crown. Ionic silver is released from the bands, which provides anti-bacterial action. In one form, a silver wire contained in the root and connected to a band and a source of direct current releases ionic silver into the surrounding tissue. In another form, the root, crown, and body have passages for accommodating drug materials and silver compounds.

36 Claims, 10 Drawing Figures

DENTAL IMPLANT

CROSS REFERENCE TO RELATED APPLICATION

This application is a continuation-in-part of U.S. patent application Ser. No. 877,073, filed Feb. 13, 1978, now U.S. Pat. No. 4,195,409.

BACKGROUND OF INVENTION

Dental implants are used to replace lost natural teeth. The implants have root structures that are attached to the jaw bone. The root structures are made of metal and acrylic materials. These materials, being relatively rigid, do not have elasticity to minimize forces on the bone and provide the implant with yielding characteristics similar to a natural tooth.

Natural teeth have biomechanical toleration and dissipation of occlusional forces. The teeth have limited movement and return to their original positions after being subjected to a force, as chewing or mastication pressure.

Carbonaceous dental implants have been proposed to approximate the modulus of elasticity of natural bone to deal with the problems of stress concentration at the bone prothesis interface. Porous polymeric material has also been proposed to serve as an artificial periodontal ligament which allows attachment of the material to bone tissue through natural tissue growth.

Dental implants are susceptible to bacterial infection of the tissue surrounding the implant. Infection in gum tissue around the base of the crown can destroy the effective use and life of the implant. Persistent infections may result in the removal of the implant.

SUMMARY OF INVENTION

The invention is directed to a prothetic implant device attachable by natural ingrowth to the tissue of a primate or animal. More specifically, the invention is directed to a dental implant which can be inserted into a mandible tooth socket and attachable to the bone by natural bone ingrowth. The dental implant includes an apparatus for supporting a dental crown on a tooth-holding bone. The apparatus has a root having first and second portions. The first portion is adapted to be attached to the crown. In one embodiment, the first portion is a truncated cone-shaped head located in a correspondingly shaped recess in the bottom of the crown. An adhesive or suitable bonding material is used to permanently attach the crown to the head. The second portion of the root extends down into a socket in the bone. An elastic body surrounds and is mounted on the second portion. A porous means surrounds the elastic body and is secured thereto. The porous means and body have a shape for filling the tooth socket, whereby bone growth occurs into the porous means to anchor the root and body to the bone.

The elastic body has yielding characteristics so that the crown and root can simulate the movements of a natural tooth subjected to chewing pressure. In one form the elastic body can be an ethylene vinyl acetate (EVA) copolymer that is bonded to the inside surface of the fabric. The fabric can be a synthetic fiber coated with a pyrolitic carbon coating or skin. The inside surface of the fabric is bonded to the elastic body.

An annular portion of the elastic body separates the upper end of the fabric from the head of the root and the crown. This permits the root and crown to have limited movement in the axial and radial directions commensurate with the movement of a natural tooth.

An object of the invention is to provide a permanent dental implant that is anchored to the tooth-holding bone by natural bone ingrowth. A further object of the invention is to provide a dental implant which provides for limited movement of the crown and root of the implant in an axial and radial direction commensurate with the movement of a natural tooth. Another object of the invention is to provide a resilient mount for a root crown of a dental implant that functions to provide the crown and root with return movement back to its original position after a sideways displacement upon release of chewing pressure.

These and other objects of the invention are embodied in the following detailed description of embodiments of the dental implant.

DETAILED DESCRIPTION OF PREFERRED EMBODIMENTS

Figure 1:
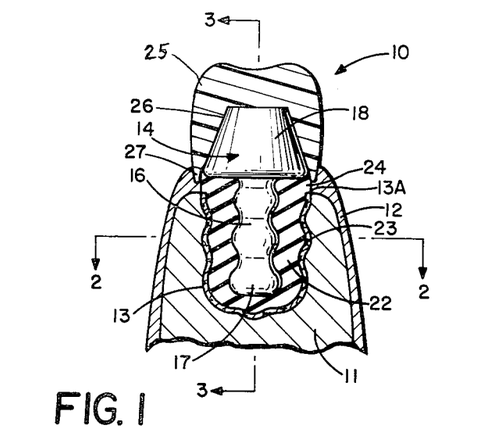
FIG. 1 is a transverse cross section of a jaw bone or human mandible provided with the dental implant of the invention.
Figure 2:
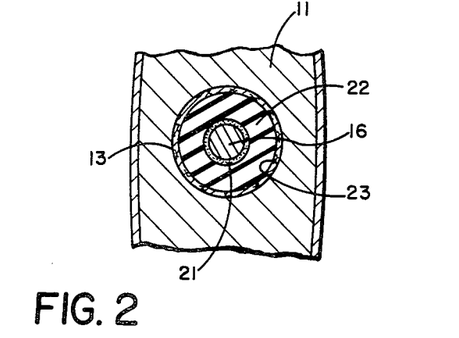
FIG. 2 is a sectional view taken along the line 2—2 of FIG. 1.

Referring to FIGS. 1 and 2, there is shown a dental implant, indicated generally at 10, located in association with the jaw bone or mandible 11 of a primate. Natural tissue or gingiva 12 covers bone 11 and surrounds mid-portion of implant 10. Bone 11 has a prepared socket or cavity 13 accommodating a portion of implant 10. During the healing process natural tissue ingrowth of the bone anchors the implant to the bone. Socket 13 has a generally cylindrical shape. Other shapes of the socket can be used to accommodate and conform to the shape of the part of the dental implant located in the socket to minimize bone loss and firmly position the implant in the socket.

Implant 10 has a root indicated generally at 14 that serves as a base or skeleton for a crown 25. Root 14 has a cylindrical body or stem 16 integrally joined to an enlarged generally cone-shaped head 18. The lower end of stem 16 has an enlarged base 17. Head 18 is a truncated cone-shaped member that is larger in diameter than the stem 16. Stem 16 extends downwardly from head 18 and has a corrugated or wave-like outer surface. Stem 16 can have other shapes, such as a smooth continuous cylindrical surface or a spiral or threaded outer surface.

Figure 3:
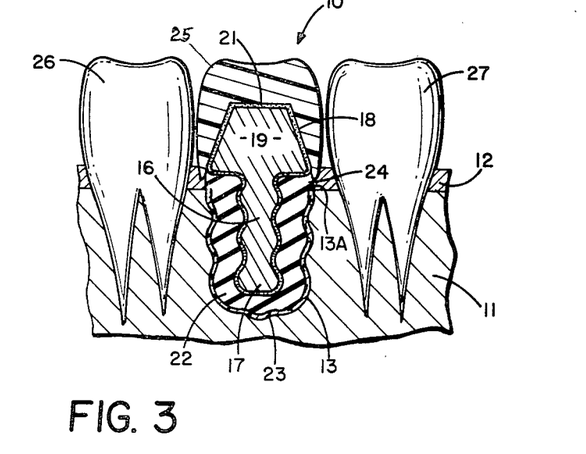
FIG. 3 is a sectional view taken along the line 3—3 of FIG. 1 showing the dental implant between two natural teeth.

Referring to FIG. 3, root 14 is a one-piece member having a base or substrate 19. Substrate 19 can be a carbon or graphite material, or a plastic material that is relatively rigid and has sufficient strength to withstand the biting and chewing. Substrate 19 is covered with an outer skin or layer 21. Preferably, layer 21 is a pyrolite carbon material positively joined to the outer surface of substrate 19. The term PYROLITE is a registered Trademark of CarboMedics, Inc., San Diego, Calif. Carbon skin 21 can have a plurality of carbon layers that are deposited on substrate 19 in a fluidized bed of hydrocarbon containing gaseous environment. The process of depositing PYROLITE carbon in this manner is disclosed in U.S. Pat. No. 3,579,645 and U.S. Pat. No. 3,971,134.

Root 14 can be made of metal, as gold, titanium, Stellite-21, a ceramic, or a plastic material. The plastic materials include polypropylene, polycarbonate and CTEE fluorocarbons.

A sleeve or body 22 surrounds stem 16. Body 22 has an upper end bonded to the lower annular surface of head 18. The thickness of body 22 is uniform around stem 16. The outer surface of body 22 is corrugated and is complimentary to the corrugated surface of stem 16. Body 22 is an elastic member providing an elastic support for the root 14. Preferably, body 22 is an ethylene vinyl acetate (EVA) copolymer. In one example, the EVA copolymer has a modulus of elasticity from $3.0 \times 10^6$ psi to $6.0 \times 10^6$ psi and a compressive strength in the direction along the axis of the root 14 of at least 200 lbs. and preferably at least 300 lbs. and a bending movement of at least 20 inch pounds and preferably at least 40 inch pounds.

Body 22 can be a plastic material, as Dow Corning Silastic, fluorosilicone rubber or a similar synthetic resinous plastic material. These materials are elastic and support root 14 for limited vertical and lateral movement. The elastic characteristic is less than the elastic characteristic of bone tissue. For example, body 22 may be about one quarter softer or more elastic than natural bone.

The outer surface of body 22 is covered with a porous cover or fabric 23. The inner surface of fabric 23 is bonded to the outer surface of body 22. The upper end of fabric 23 is spaced from the head 18 so that an annular portion 24 of the body 22 is between the lower edge of crown 25 and fabric 23. Fabric 23 fits into the socket 13 and bone 11. Fabric 23, being porous, allows attachment of the fabric to the bone tissue through the natural tissue growth of the bone. Fabric 23 can be a modified synthetic fiber, as Nylon or Teflon fibers or similar biologically inert material. The fabric is coated with a pyrolite carbon coating or skin. The coated fabric 23 has a pore or space structure which permits a bone tissue attachment, while inhibiting calcification of the bone. The pore size is preferably between the range of 20 to 50 microns. The fabric 23 has a thickness of at least 0.01 mm. with only the inside surface of the fabric bonded to body 22.

Fabric 23 is bonded to body 22 by placing body material in an uncured state and fabric 23 in a mold. The fabric surrounds the uncured body material. Pressure and heat is applied to the mold to melt or cure the body material, as EVA copolymer. An example of this process is disclosed in U.S. Pat. No. 3,579,645 and U.S. Pat. No. 3,971,134.

In use, as shown in FIG. 3, implant 10 is located between teeth 26 and 27, with stem 16 and body 22 positioned in socket 13 formed in bone 11. Fabric 23 is held in firm engagement with the walls of the socket 13 by the elastic body 22. Body 22 can be under slight compression as it is forced into socket 13. The upper end or edge 13A of fabric 23 is at approximately the bone level below tissue 12. Crown 25 has a truncated cone-shaped cavity 26 that accommodates head 18 of root 14. Suitable adhesives or cements are used to attach crown 25 to head 18. The lower edge 27 of crown 25 is in engagement with an annular portion of the upper end of elastic body 22. The lower edge 27 of crown 25 is also spaced from bone 11 and the upper end of fabric 23.

The elastic body 23 allows root 14 and crown 25 mounted thereon limited movement axially and radially commensurate with the movement of a natural tooth. Crown 25 will return to its original position after a sideways displacement as soon as the chewing pressure has been released from the crown. Elastic body 22 provides for an even distribution of the forces on the fabric 23, thereby applying a minimum of concentration of forces at any particular area of the fabric. This maintains interface between fabric 23 and the natural bone of the tooth socket. This fabric 23 will be attached to the bone tissue through the natural growth over a period of time. The dissipation of and dampening of the forces that are placed on crown 25 with elastic body 22 eliminates the abnormal stresses on the fabric 23 which would affect the tissue ingrowth into fabric 23. Fabric 23 being coated with pyrolite carbon, is compatible with the bone tissue and does not deteriorate in time. The carbon coating of the fabric also increases the strength of the fabric 23.

Referring to FIGS. 4-7, there is shown a modification of the dental implant of the invention indicated generally at 100, located in association with the jaw bone or mandible 101 of a primate, as man. Natural gum tissue or gingiva 102 covers bone 101. Tissue 102 has an annular portion that surrounds the base of the crown 108 of the implant. Implant 100 is located in a socket or cavity 103 extended down into the bone 101. In time, during the healing process, natural tissue ingrowth of the bone anchors the implant to the bone. The socket 103 has a generally cylindrical shape and extends down into the bone to locate the implant in alignment with adjacent associated teeth.

Implant 100 has a core or root indicated generally at 104 comprising a generally cylindrical stem 106 joined to an enlarged head 107. A crown 108 is secured to head 107 with an adhesive or cement material. Crown 108 has a cavity or opening 109 having a generally truncated cone shape that is complimentary to the truncated cone shape of head 107. Head 107 and cavity 109 in crown 108 can have other shapes.

Figure 5:
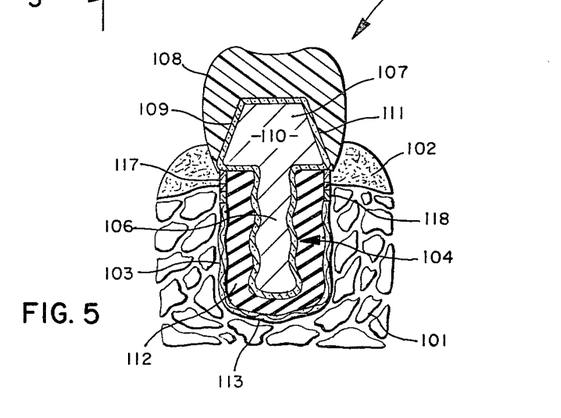
FIG. 5 is a cross section on a reduced scale taken along the line 5—5 of FIG. 4.
Figure 6:
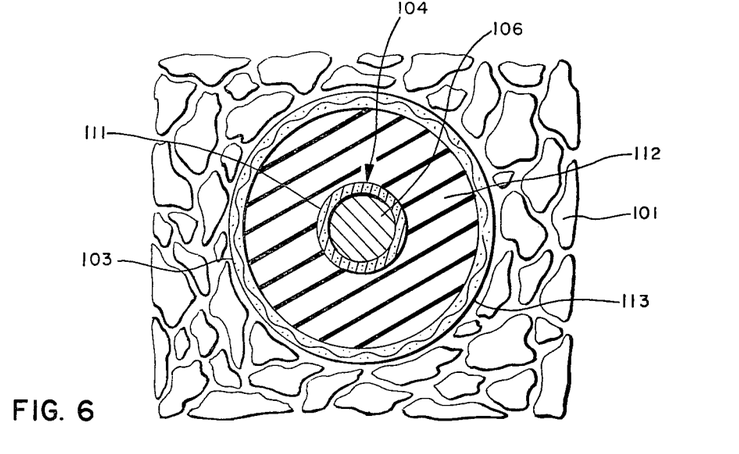
FIG. 6 is a sectional view taken along the line 6—6 of FIG. 5.
Figure 7:
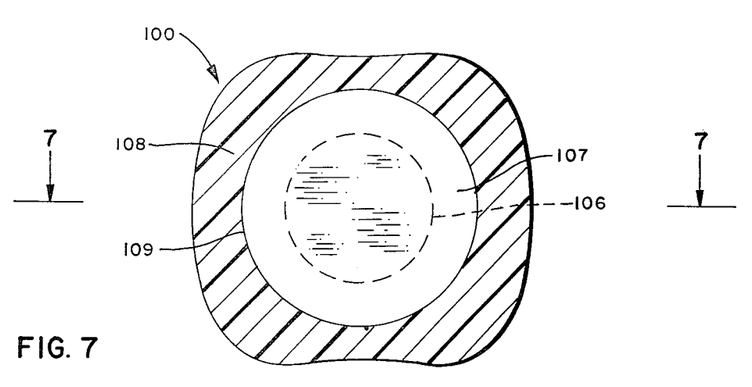
FIG. 7 is a sectional view taken along the line 7—7 of FIG. 5.

As shown in FIG. 5, root 104 is a one-piece member having a base or substrate 110 covered with a coating or outer layer 111. Base 110 can be carbon or graphite material or a plastic material that is relatively rigid and has sufficient strength to withstand the biting and chewing forces. The outer skin 111 is a PYROLITE carbon material positively joined to the outer surface of substrate 110. Carbon skin 111 can have a plurality of carbon layers that are deposited on substrate 111 in a fluidized bed of hydrocarbon containing gases. The process of depositing pyrolitic carbon in this manner is disclosed in U.S. Pat. Nos. 3,579,645 and 3,971,134.

An annular sleeve or body 112 surrounds stem 106 and engages the surface of head 107. Body 112 is a compressible elastic material that provides an elastic support for the root 104. Preferably, body 112 is an ethylene vinyl acetate (EVA) copolymer. Body 112 can be made of the same material and have the same characteristics as body 22, as shown in FIGS. 1–3 hereinbefore described. Body 112 has a generally uniform thickness and extends entirely around stem 106 and around the bottom of the stem. The upper edge of body 112 engages and is secured to the annular lower face of head 107.

The outer surface of body 112 is covered with a porous cover or fabric 113. The inner surface of fabric 113 is bonded or permanently secured to the outer surface of body 112. During the bonding process body 112 does not inhibit the porosity or extend into the pores or spaces of the fabric. The fabric 113, being porous, allows ingrowth of bone tissue by the natural growth of the bone. Fabric 113 can be a modified synthetic fiber, as Nylon or Teflon fibers or similar biologically inert material. In one form, the fabric can be coated with a pyrolitic carbon coating or skin. The coated fabric has pores or space structure which permits bone tissue attachment while inhibiting calcification of the bone. The pore or space size of the fabric is preferably between a range of 20 to 50 microns. The fabric has a thickness of at least 0.01 mm. with only the inside surface of the fabric bonded to the elastic body 112.

Figure 4:
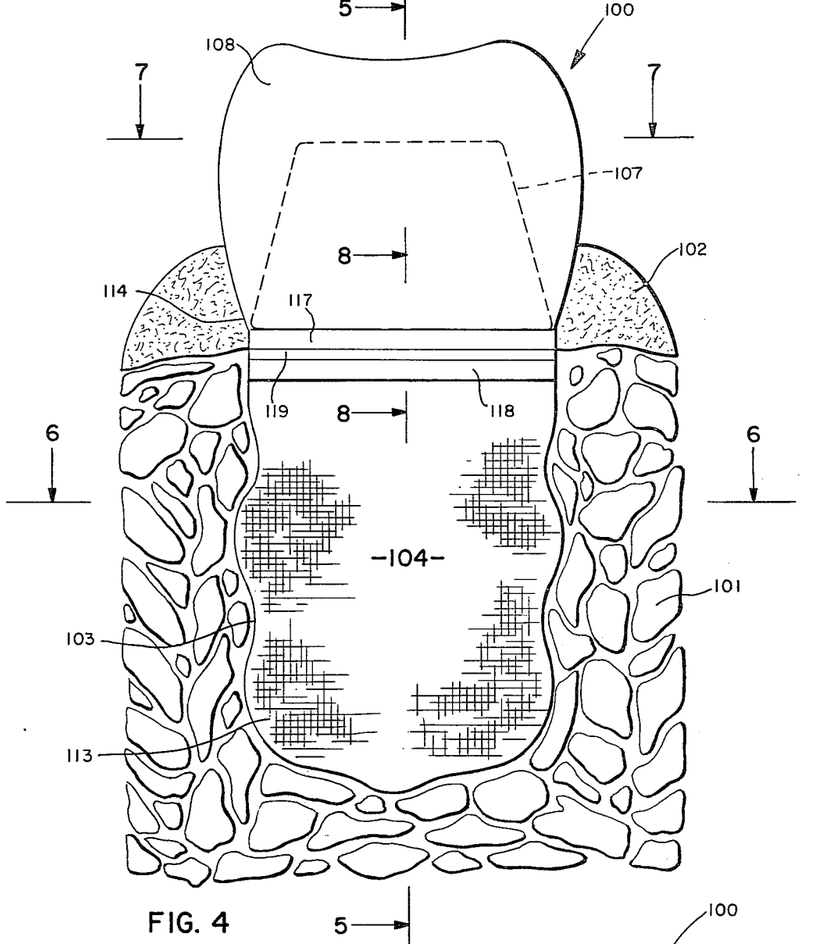
FIG. 4 is a side elevational view of a modification of the dental implant located in the jaw bone.
Figure 8:
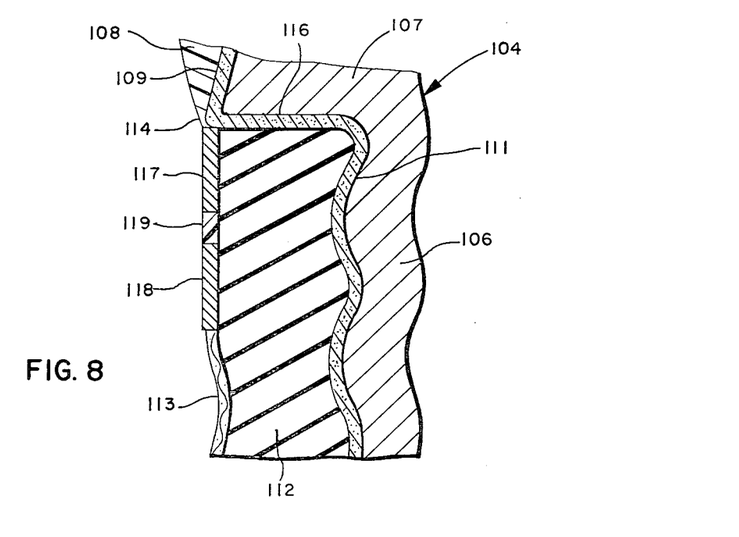
FIG. 8 is an enlarged sectional view taken along the line 8—8 of FIG. 4.

As shown in FIGS. 4 and 8, crown 108 has an annular lower edge or lip 114 that surrounds and is generally aligned with the lower edge 116 of head 107. A first cylindrical metal band 117 surrounds the upper end of body 112. The upper edge of band 117 engages lip 114 and head edge 116. Band 117 and the outer surface of lip 114 of crown 108 have smooth substantially continuous coextensive surfaces which inhibit the collection of foreign material and sites for bacterial growth. A second band 118 surrounds body 112 below band 117. An annular rib or elastic material 119 separates bands 117 and 118. The fabric cover 113 engages the lower edge of band 118. Bands 117 and 118 are bonded to body 112. Bands 117 and 118 can contain silver or silver compounds which release silver ions providing antibacterial action. Bands 117 and 118 can be dissimilar materials, as silver and gold, which provide galvanic action which enhances the releasing and flow of silver ions into the tissue 103 surrounding the implant.

The silver and gold can be vacuum deposited onto the elastic body 112 by a sputtering process. As another alternative, each band 117 and 118 can be coated with a segment of silver and a segment of gold. Silver and gold are used by way of example. Other metals, as aluminum, copper, zinc, and alloys as silver-zinc-allantoinate, silver sulfadiazine, and the like may be used. When silver is used, silver ions disperse, penetrate, and move through the bone and gum tissue around the implant producing beneficial antiseptic results and bactericidal and germicidal action.

FIG. 8 shows bands 117 and 118 as solid cylindrical bands surrounded and bonded to sleeve or body 112. The number of bands can vary and different combinations of metals may be used. The bands 117 and 118 can be a continuous single band of silver or silver-carrying material. The bands 117 and 118 can be sprayed metal particles onto the upper annular outer surface of body 112.

Figure 9:
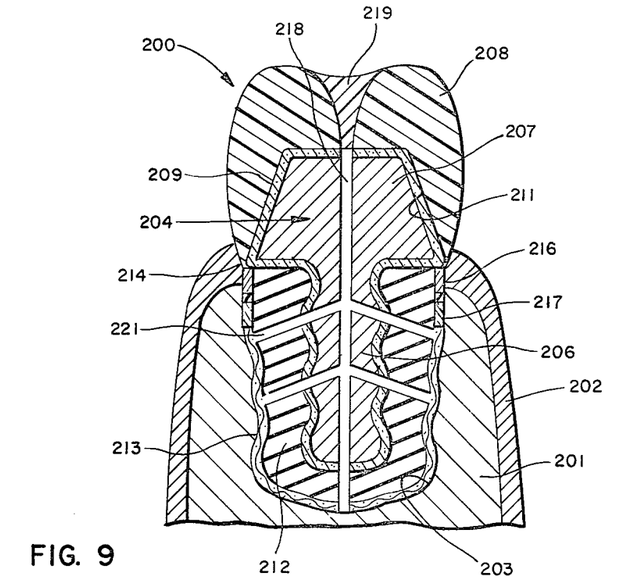
FIG. 9 is a cross sectional view of a further modification of the dental implant similar to FIG. 3.

Referring to FIG. 9, there is shown another modification of the dental implant indicated generally at 200 located in a jaw bone 201 surrounded by natural tissue 202. Jaw bone 201 has a socket 203 accommodating the root of the dental implant 200.

Implant 200 has a generally cylindrical root indicated generally at 204 comprising a downwardly directed rod-like stem 206 joined to a top member or head 207. The implant 200 has a crown 208 having a truncated cone-shaped opening or cavity 209 surrounded by and secured to the truncated shaped head 207. Root 207 has an outer layer of coating 209 of biologically inert material, such as pyrolitic carbon. The root 204 can be a one-piece metal or plastic member.

An elastic sleeve or body 212 surrounds stem 206. Body 112 has a generally uniform thickness and surrounds the sides and the ends of stem 206. The upper portion of body 211 engages and is secured to an annular bottom surface of head 207. A porous cover or fabric 213 surrounds and is bonded to the outer surface of body 212. The fabric 213 can be the same as the fabrics 23 and 113 previously described.

Crown 208 has a lower annular edge 214 surrounding the lower edge of head 207. Lower edge 214 of crown 208 is located in engagement with a downwardly extended annular band 216. Band 216 surrounds and is secured to the upper portion of body 212. Located below and spaced from band 216 is a second band 217. Band 217 surrounds and is secured to the body 212. Bands 216 and 217 may be of the same or dissimilar materials; for example, silver and gold, which release metal ions that have advantageous anti-bacterial action.

The crown 208 and root 204 have a longitudinal main passage 218 closed at its upper end with a plug 219. A plurality of lateral passages 221 extend outwardly from the main passage 218. The passages 218 and 221 can accommodate drug materials or silver compounds to provide for continuous long-term administration of drug materials to bone 201 and gum tissue 202 surrounding implant 200.

Figure 10:
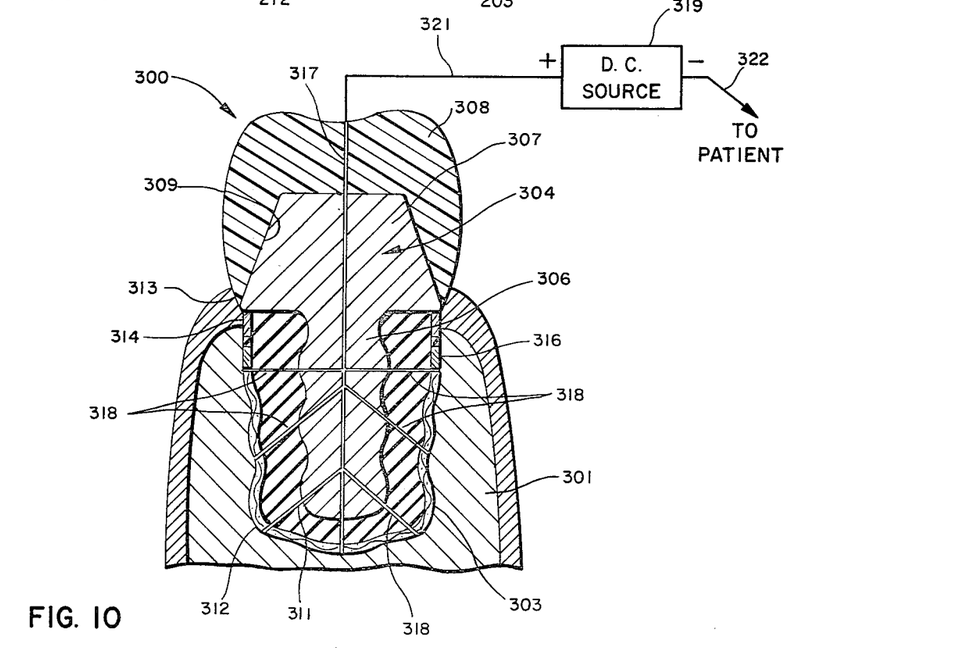
FIG. 10 is a sectional view of another modification of the dental implant similar to FIG. 9.

Referring to FIG. 10, there is shown a further modification of the dental implant of the invention indicated generally at 300 attached to a bone 301 surrounded with the natural tissue 302. Implant 300 is located within a cylindrical socket 303 in bone 301. Implant 300 has a root 304 having a generally cylindrical stem 306 joined to a truncated cone-shaped head 307. A crown 308 surrounds and is secured to head 307. Crown 308 has a bottom opening or cavity 309 accommodating head 307.

A resilient or elastic sleeve or body 311 surrounds stem 306 and is covered with a porous cover or fabric 312. The inner surface of fabric 312 is continuously bonded to the outer surface of body 311. Fabric 312 is the same as the fabric 23, 113, and 213 previously described.

The crown 308 has a lower annular edge 313 that surrounds the lower edge of the head 307. A plurality of metal bands 314 and 316 surround the body 311 adjacent the lower edge 313. The bands 314 and 316 can be the same or dissimilar metals, including silver and silver compounds, as previously described with respect to bands 117 and 118, as shown in FIGS. 4 and 8.

A longitudinal wire 317, such as silver wire, extends down through crown 308 and root 304. Wire 317 extends to the bottom of fabric 312. A plurality of lateral or spur wires 318 are connected to the longitudinal wire 317 and extend to the fabric 312. The wires 318 also extend to and join to the metal band 316. Additional wires may be used to connect the central longitudinal wire 317 to the band 314.

A D.C. power source 319 is connected with a line or cable 321 to the top of wire 317. The opposite side of power source 319 is connected with a line or cable 322 to the patient. A suitable grounding electrode (not shown) joined to line 322 completes the circuit to the patient. When the D.C. current is caused to flow through wires 317 and 318 and band 316, the wires 317 and 318 and band 316 function as electrodes causing bactericidal silver ions to be released to the bone tissue and skin tissue 302 approximate the implant. The silver ion activity continues at a low level indefinitely after the D.C. power source is disconnected from wire 317.

While there has been shown and described preferred embodiments of dental implants, changes in the materials, sizes, and dimensions of the parts of the dental implant can be made by those skilled in the art without departing from the invention. The invention is defined in the following claims.

The embodiments of the invention in which an exclusive property or privilege is claimed are defined as follows:

1. A prothesis for dental replacement in a living body comprising: a root having a head and a stem; a crown attached to the head; an elastic body surrounding and mounted on the stem; porous means surrounding the elastic body and secured thereto, said porous means and elastic body having a shape for insertion into a mandible tooth socket whereby bone growth into the porour means anchors the root to the bone; and means surrounding the elastic body adjacent the crown for inhibiting infection of bone and tissue adjacent the prothesis.

2. The prothesis of claim 1 wherein: the means surrounding the elastic body comprises a plurality of metal bands.

3. The prothesis of claim 2 wherein: the bands are of dissimilar metals.

4. The prothesis of claim 2 wherein: some of the bands include silver.

5. The prothesis of claim 1 wherein: the means surrounding the elastic body comprises a pair of annular metal bands.

6. The prothesis of claim 5 wherein: one band contains silver.

7. The prothesis of claim 1 including: electrical conductor means extended into the root and to the porous means adapted to be connected to an electrical power source.

8. The prothesis of claim 7 wherein: the conductor means is connected to the means surrounding the elastic body.

9. The prothesis of claim 1 including: passage means in the root and elastic body to accommodate drug materials.

10. The prothesis of claim 1 wherein: the porous means is a fabric surrounding the body and bonded thereto, said fabric being separated from the head.

11. The prothesis of claim 10 wherein: the elastic body engages the head and has a generally uniform thickness around the stem.

12. The prothesis of claim 10 wherein: the fabric has an inside surface and the body has an outside surface, said inside surface being bonded to the outside surface of the body.

13. An apparatus for supporting a dental crown on a tooth holding bone comprising: a root having a first portion and a second portion, said first portion adapted to be attached to the crown; an elastic body mounted on the second portion; porous means surrounding the body and secured thereto, said porous means and body having a shape for insertion into a bone tooth socket whereby bone growth into the porous means anchors the root to the bone; and means surrounding the second portion of the elastic body for inhibiting infection of bone and tissue surrounding the porous means.

14. The apparatus of claim 13 including: at least one layer of pyrolite carbon covering the porous means.

15. The apparatus of claim 13 wherein: porous means is a fabric surrounding the body and bonded thereto, said fabric being separated from the first portion.

16. The apparatus of claim 15 wherein: the elastic body engages the first and second portions of the root and has a generally uniform thickness around the second portion of the root.

17. The apparatus of claim 13 wherein: the means surrounding the elastic body comprises a plurality of metal bands.

18. The apparatus of claim 17 wherein: the metal bands are of dissimilar metals.

19. The apparatus of claim 17 wherein: some of the bands include silver.

20. The apparatus of claim 13 wherein: the means surrounding the elastic body comprises a pair of spaced annular metal bands.

21. The apparatus of claim 20 wherein: at least one band contains silver.

22. The apparatus of claim 13 including: electrical conductor means extended into the root and to the porous means adapted to be connected to an electrical power source.

23. The apparatus of claim 22 wherein: the conductor means is connected to the means surrounding the elastic body.

24. The apparatus of claim 13 including: passage means in the root and elastic body to accommodate drug materials.

25. An apparatus for supporting a member in a bone of a living body comprising: rigid means having a first portion and a second portion, said first portion adapted to be attached to the member; an elastic body mounted on the second portion; porous means surrounding the body and secured thereto, said porous means and body having a shape for insertion into a cavity in the bone whereby bone growth into the porous means anchors the rigid means to the bone; and means surrounding the second portion of the rigid means for inhibiting infection of bone and tissue adjacent the apparatus.

26. The apparatus of claim 25 including: at least one layer of pyrolite carbon covering the porous means.

27. The apparatus of claim 25 wherein: porous means is a fabric surrounding the body and bonded thereto, said fabric being separated from the first portion.

28. The apparatus of claim 27 wherein: the elastic body engages the first and second portions of the rigid means and has a generally uniform thickness around the second portion of the rigid means.

29. The apparatus of claim 25 wherein: the means surrounding the elastic body comprises a plurality of metal bands.

30. The apparatus of claim 29 wherein: the bands are of dissimilar metals.

31. The apparatus of claim 30 wherein: some of the bands include silver.

32. The apparatus of claim 25 wherein: the means surrounding the elastic body comprises a pair of spaced annular metal bands.

33. The apparatus of claim 32 wherein: at least one of the bands contains silver.

34. The apparatus of claim 25 including: electrical conductor means extended into the root and to the porous means adapted to be connected to an electrical power source.

35. The apparatus of claim 34 wherein: the conductor means is connected to the means surrounding the elastic body.

36. The apparatus of claim 25 including: passage means in the root and elastic body to accommodate drug materials.

* * * * *

UNITED STATES PATENT AND TRADEMARK OFFICE
CERTIFICATE OF CORRECTION

PATENT NO. : 4,252,525
DATED : February 24, 1981
INVENTOR(S) : Frank W. Child

It is certified that error appears in the above-identified patent and that said Letters Patent are hereby corrected as shown below:

Column 4, line 15, "23" should be --22--.

Column 7, line 31, "porour" should be --porous--.

Signed and Sealed this

Second Day of June 1981

[SEAL]

Attest:

RENE D. TEGTMEYER

Attesting Officer

Acting Commissioner of Patents and Trademarks